(12) United States Patent
Meoni

(10) Patent No.: US 10,953,116 B2
(45) Date of Patent: Mar. 23, 2021

(54) ASSEMBLY FOR SMOOTHING AND THROTTLING A GASEOUS STREAM

(71) Applicant: I.M.A. INDUSTRIA MACCHINE AUTOMATICHE S.P.A IN SIGLA IMA S.P.A., Ozzano Dell'Emilia (IT)

(72) Inventor: Eddi Meoni, Ozzano Dell'Emilia (IT)

(73) Assignee: I.M.A. INDUSTRIA MACCHINE AUTOMATICHE S.P.A IN SIGLA IMA S.P.A., Ozzano Dell'Emilia (IT)

(*) Notice: Subject to any disclaimer, the term of this patent is extended or adjusted under 35 U.S.C. 154(b) by 216 days.

(21) Appl. No.: 16/085,729

(22) PCT Filed: Mar. 16, 2017

(86) PCT No.: PCT/IB2017/051539
§ 371 (c)(1),
(2) Date: Sep. 17, 2018

(87) PCT Pub. No.: WO2017/158552
PCT Pub. Date: Sep. 21, 2017

(65) Prior Publication Data
US 2019/0111167 A1 Apr. 18, 2019

(30) Foreign Application Priority Data
Mar. 17, 2016 (IT) .................. 102016000027865

(51) Int. Cl.
*A61L 2/00* (2006.01)
*B03C 3/00* (2006.01)
(Continued)

(52) U.S. Cl.
CPC .................. *A61L 2/06* (2013.01); *A61L 2/20* (2013.01); *A61L 2/26* (2013.01)

(58) Field of Classification Search
CPC ......... A61L 9/00; A61L 9/16; A61L 2209/134
(Continued)

(56) References Cited

U.S. PATENT DOCUMENTS

| 5,313,375 A | 5/1994 | Jones |
| 2005/0158219 A1 | 7/2005 | Taylor et al. |

(Continued)

FOREIGN PATENT DOCUMENTS

| CN | 1094806 A | 11/1994 |
| CN | 103032116 A | 4/2013 |

(Continued)

OTHER PUBLICATIONS

International Search Report dated Nov. 6, 2017 re: Application No. PCT/IB2017/051539, pp. 1-4, citing: EP 1 864 840 A1, US 2005/158219 A1, WO 2013/116630 A2, DE 42 33 834 C1 and WO 2006/075227 A2.

(Continued)

*Primary Examiner* — Monzer R Chorbaji
(74) *Attorney, Agent, or Firm* — Cantor Colburn LLP

(57) ABSTRACT

An assembly for smoothing and throttling a gaseous stream, which can be installed downstream of a region of discontinuity between areas of controlled outflow of the gas, includes an aerodynamic guide that is substantially teardrop-shaped. The assembly further includes at least one baffle that faces and is proximate to at least one respective surface of the aerodynamic guide. The baffle has the face directed toward the surface of the guide substantially similar in shape to that of the surface.

9 Claims, 4 Drawing Sheets

(51) Int. Cl.
*A61L 2/06* (2006.01)
*A61L 2/20* (2006.01)
*A61L 2/26* (2006.01)

(58) Field of Classification Search
USPC ............... 422/120–121, 291, 308; 96/60, 64
See application file for complete search history.

(56) References Cited

U.S. PATENT DOCUMENTS

| | | | | |
|---|---|---|---|---|
| 2007/0283810 | A1* | 12/2007 | Besi | B03C 3/08 96/64 |
| 2016/0016457 | A1 | 1/2016 | Caliendo et al. | |

FOREIGN PATENT DOCUMENTS

| | | |
|---|---|---|
| CN | 105526641 A | 4/2016 |
| DE | 4233834 C1 | 11/1993 |
| DE | 4306399 A1 | 9/1994 |
| EP | 1864840 A1 | 12/2007 |
| JP | H07005856 Y | 10/1993 |
| WO | 2006075227 A2 | 7/2006 |
| WO | 2013116630 A2 | 8/2013 |
| WO | 2016010740 A1 | 1/2016 |

OTHER PUBLICATIONS

IT Search Report dated Nov. 7, 2016 re: Application No. IT UA20161748, pp. 1-9, citing: EP 1 864 840 A1, US 2005/158219 A1, WO 2013/116630 A2, DE 42 33 834 C1 and WO 2006/075227 A2.

Written Opinion dated Nov. 6, 2017 re: Application No. PCT/IB2017/051539, pp. 1-7, citing: EP 1 864 840 A1, US 2005/158219 A1, WO 2013/116630 A2 and DE 42 33 834 C1.

EU Notice of Reasons of Refusal dated Dec. 9, 2020 re: Application No. 2018-544106, pp. 1-6, citing: U.S. Pat. No. 5,313,375, DE 4308399, U.S. Appl. No. 2007/0283810, U.S. Appl. No. 2016/0016457, JP H07-005856 Y and CN 105526641.

* cited by examiner

ASSEMBLY FOR SMOOTHING AND THROTTLING A GASEOUS STREAM

TECHNICAL FIELD

The present disclosure relates to an assembly for smoothing and throttling a gaseous stream, in particular the purpose of the assembly according to the disclosure is to reduce to the minimum (ideally eliminate) the turbulence that is generated within a stream of gas (for example air), by rendering such stream perfectly laminar or comparable to a laminar stream.

BACKGROUND

In various sectors of the art, the need arises to strike appropriate components with a stream of gas in order to subject them to a specific treatment.

For example, in dryers, a stream of warm air is used to strike specific components that need to be dried after having been subjected to washing operations.

Similarly, in high-temperature sterilizers, the components to be treated are conveyed into a chamber in which a stream of high-temperature air is maintained, and this results in a superheating of the components with consequent sterilization thereof (if they remain inside the chamber for a preset time).

The creation of the stream of gas in the operating chamber is in any case obtained by way of a ventilation apparatus (arranged, for example, downstream of a heat exchanger or of a heater) which sends the gas to a circulation hood that surmounts the chamber.

By suitably selecting the dimensions and the geometries of the circulation hood, with respect to the volume of the chamber and to the speed and flow-rate of the stream of gas introduced, it is possible to ensure that the stream of gas that will strike the components to be processed is laminar.

More often, partitions are interposed between the circulation hood and the chamber in order to control and laminate the stream of gas.

If the chamber is very large, it will therefore be necessary to arrange a plurality of partitions side by side, because they have preset dimensions and it would not make economic sense to provide a single partition of identical shape and dimensions to those of the chamber.

The partitions will therefore be arranged side-by-side so as to be distributed in order to provide an upper wall of the continuous chamber; the partitions, in order to be capable of assuming such configuration, must be supported by a frame.

Obviously, at the discontinuity surface between two contiguous partitions, a region will be defined in which the stream of gas will not be correctly subjected to lamination and therefore incidences of turbulence may be created which are negative for the treatment to be carried out on the components present in the chamber.

In order to minimize such problems and ensure that the entire stream of air that will strike the components to be processed is substantially laminar, it is known to arrange aerodynamic guides (with a substantially teardrop-shaped profile) below the frame, at the portions of discontinuity between two contiguous guides.

The stream of gas that exits from the edge of a partition, thanks to the presence of such aerodynamic guides, follows a surface of the guide remaining laminar and joins the stream that flows over the opposite face of the guide (originating from the contiguous partition) without causing turbulence.

In reality the flow is not laminar but still has some turbulence which is generated at the meeting point of the two currents originating from opposite faces of a same aerodynamic guide.

In some specific applications, even the minimal presence of turbulent motion of the gases conveyed can be negative and/or counterproductive, demonstrating that the adoption of aerodynamic guides with teardrop-shaped profile is, effectively, insufficient to create laminar streams of gas that meet requirements.

SUMMARY

The aim of the present disclosure is to solve the above mentioned drawbacks, by providing an assembly for smoothing and throttling a gaseous stream that minimizes the turbulence that is generated at the outflow of gas along discontinuity surfaces.

Within this aim, the present disclosure provides an assembly for smoothing and throttling a gaseous stream that has a shape structure that is compatible with conventional technical solutions.

The present disclosure also provides an assembly for smoothing and throttling a gaseous stream that is more efficient than conventional aerodynamic guides.

The present disclosure further provides an assembly for smoothing and throttling a gaseous stream that is low cost, easily and practically implemented and safe in use.

This aim and these and other advantages which will become better apparent hereinafter are achieved by providing an assembly for smoothing and throttling a gaseous stream, of the type that can be installed downstream of a region of discontinuity between areas of controlled outflow of said gas and which comprises an aerodynamic guide that is substantially teardrop-shaped, characterized in that it comprises at least one baffle that faces and is proximate to at least one respective surface of said aerodynamic guide, said baffle having the face directed toward said surface of said guide substantially similar in shape to that of said surface.

BRIEF DESCRIPTION OF THE DRAWINGS

Further characteristics and advantages of the disclosure will become better apparent from the detailed description that follows of a preferred, but not exclusive, embodiment of the assembly for smoothing and throttling a gaseous stream according to the disclosure, which is illustrated by way of non-limiting example in the accompanying drawings, wherein.

DETAILED DESCRIPTION OF THE DRAWINGS

Figure 1:
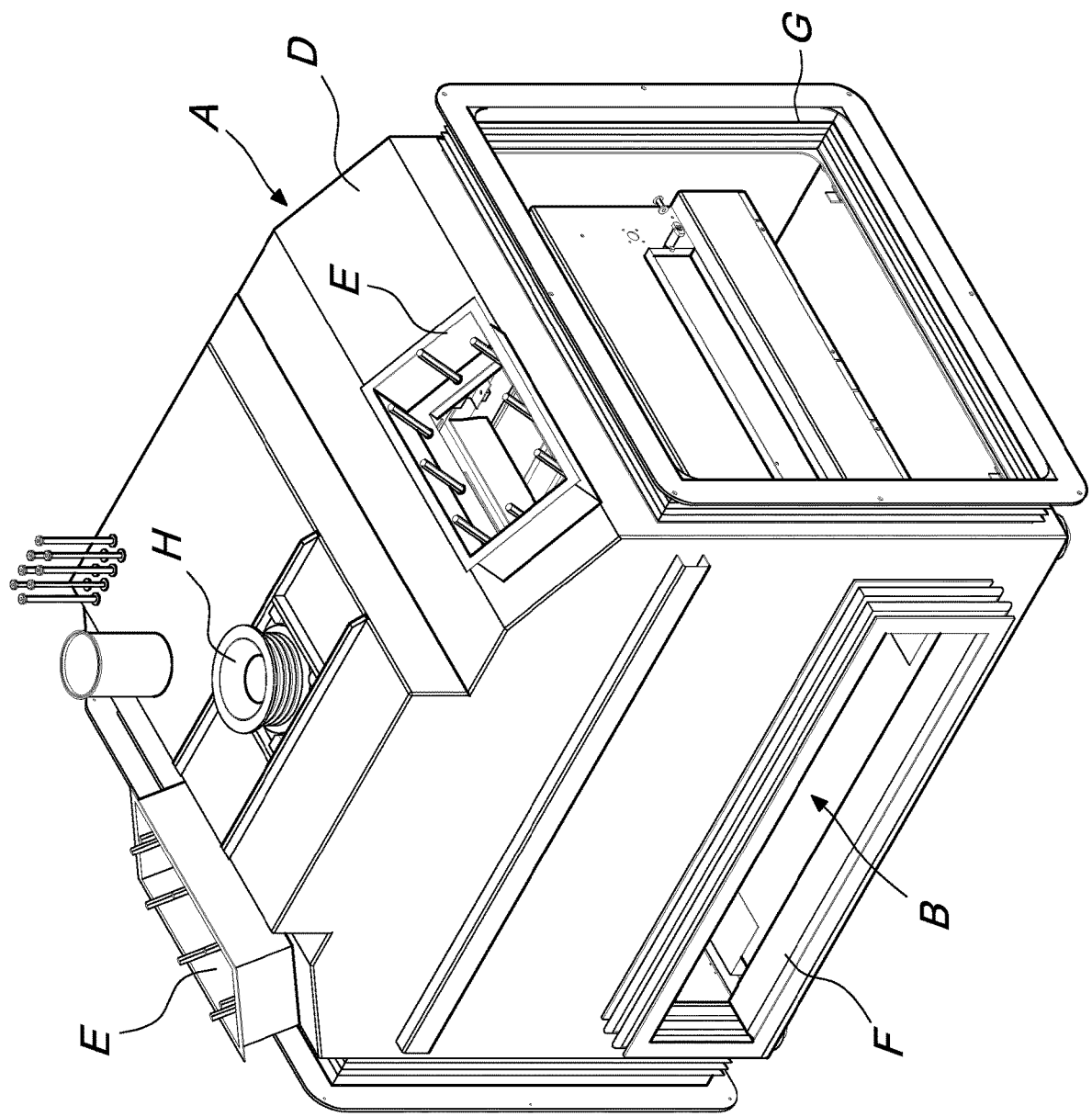
FIG. 1 is a perspective view of an apparatus for circulating a stream of gas, which comprises an assembly for smoothing and throttling a gaseous stream according to the disclosure.

With reference to the figures, the reference numeral 1 generally designates an assembly for smoothing and throttling a gaseous stream.

It has been explained that in several sectors apparatuses A are used which are adapted to circulate a gaseous stream. These can be dryers, in which a stream of warm air strikes specific components that need to be dried after having been subjected to washing operations, and/or high-temperature sterilizers, in which the components to be treated are conveyed into an inner chamber in which a stream of high-temperature air is maintained, resulting in a superheating of the components with consequent sterilization thereof (if they remain inside the chamber for a preset time).

In any case, this type of apparatus A creates, by way of a ventilation apparatus (not shown), a stream of gas that passes from a circulation chamber C into an operating chamber B after having passed through adapted aerodynamic throttling partitions 4 interposed between the circulation chamber C and the operating chamber B.

In the example shown, the fan is arranged in the circulation chamber C underlying a hood D that surmounts the chamber B.

The hood D is provided with a pair of windows E in which are mounted heating means (not shown) that are adapted to heat the gas in the circulation chamber C.

The assembly 1 for controlling and laminating a gaseous stream can be installed between the circulation chamber C and the operating chamber B, downstream of a discontinuity surface between areas of controlled outflow of the gas.

The accompanying figures refer to an apparatus constituted by a sterilizer that has a first and a second opening F, mutually opposite, for the passage of a conveyor belt on which are arranged the components to be subjected to the high-temperature gaseous stream. The belt passes through the operating chamber B inside which the treatment occurs. There are further two mutually opposite windows G arranged at the sides of the sterilizer.

Figure 2:
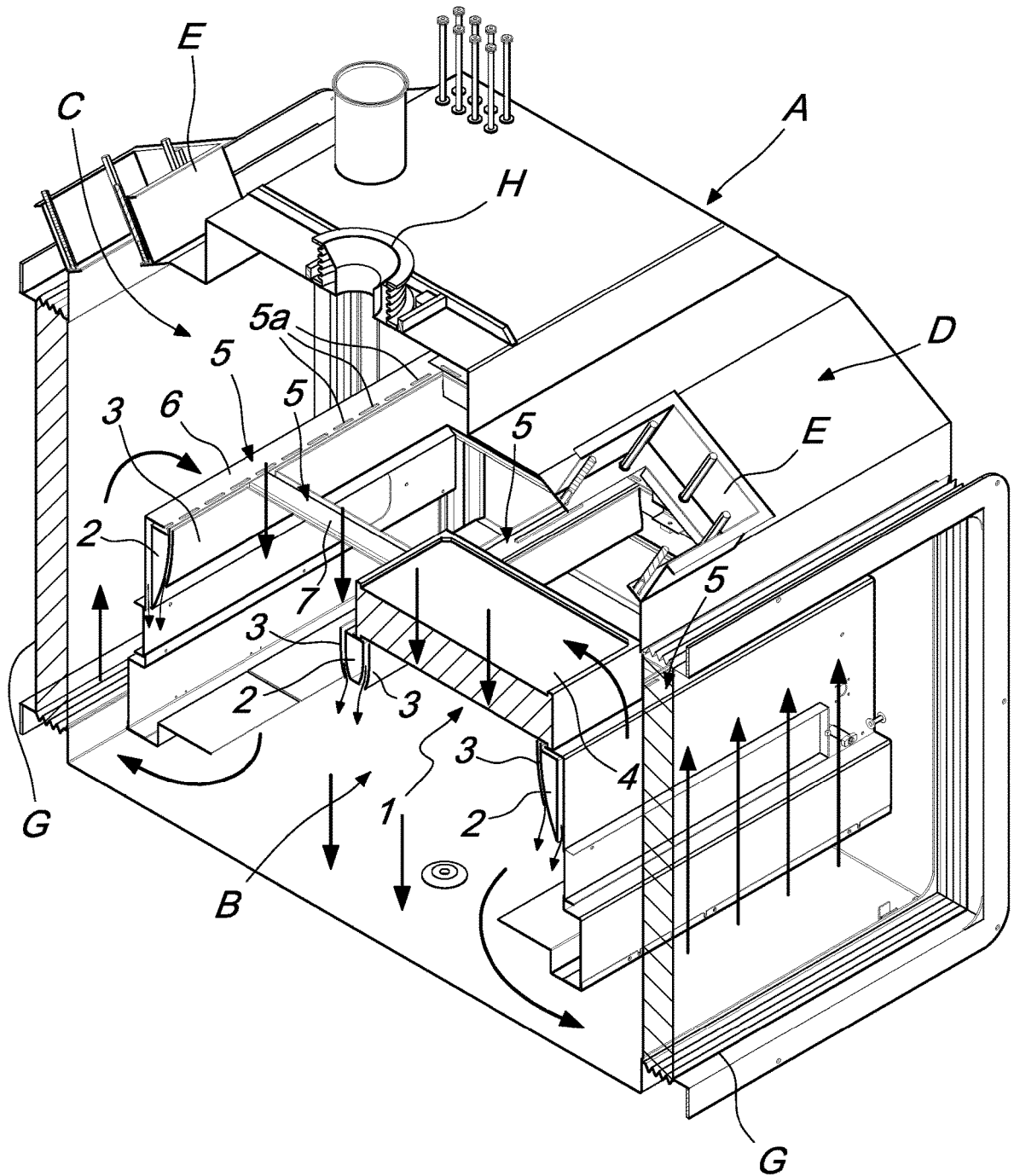
FIG. 2 is a cross-sectional perspective view taken along a transverse plane of the apparatus of FIG. 1 which comprises an assembly according to the disclosure.
Figure 3:
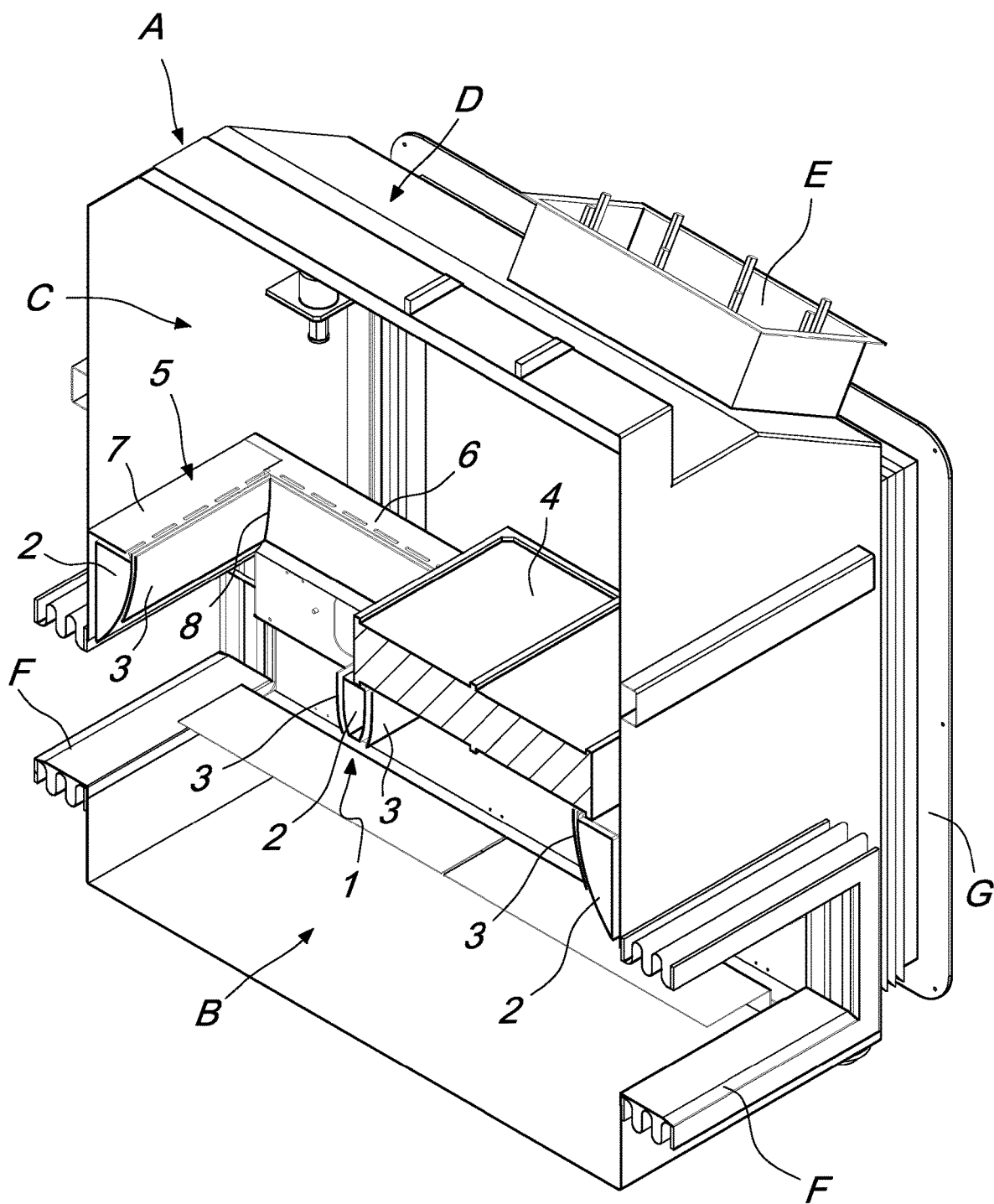
FIG. 3 is a cross-sectional perspective view taken along a longitudinal plane of the apparatus of FIG. 1 which comprises an assembly according to the disclosure.
Figure 4:
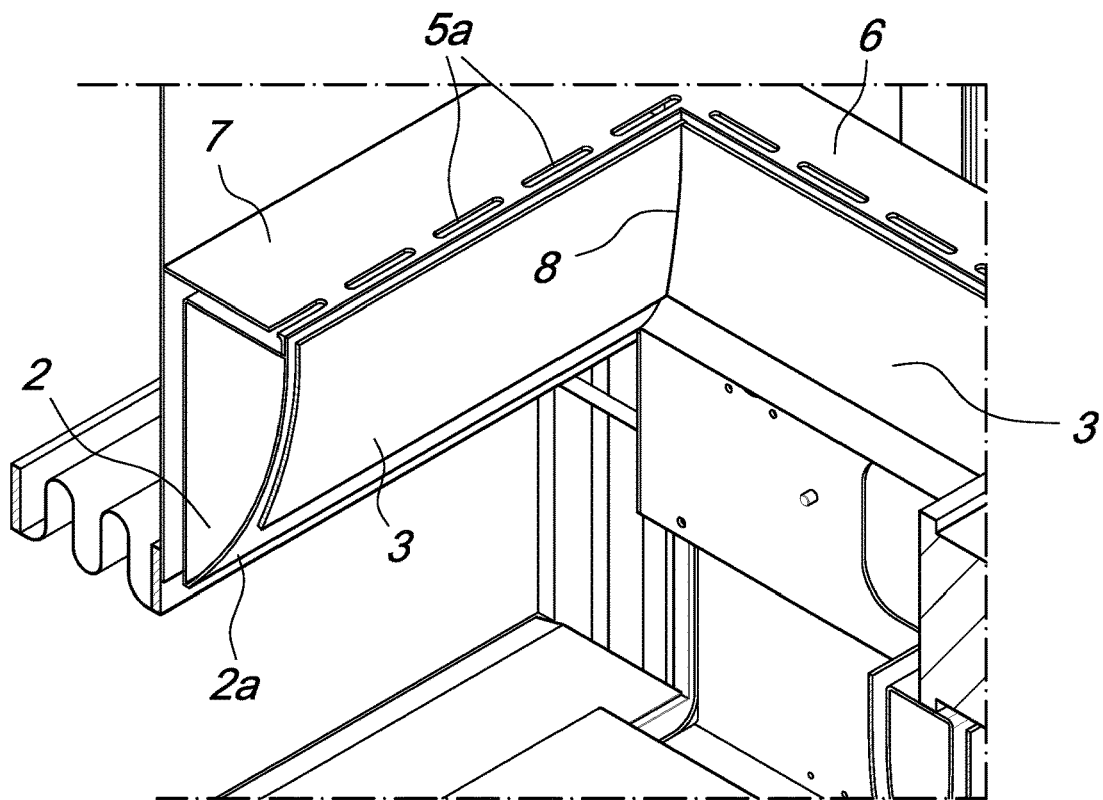
FIG. 4 is an enlarged view of a first detail of FIG. 3.
Figure 5:
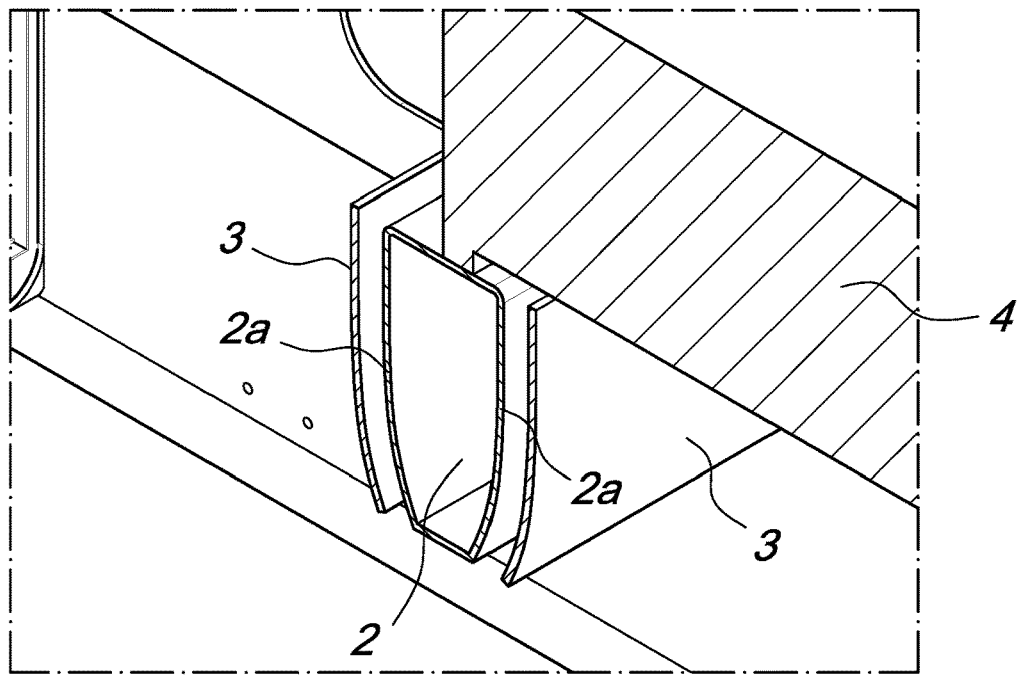
FIG. 5 is an enlarged view of a second detail of FIG. 3.

The arrows in FIG. 2 indicate the path of the stream of gas that rise from the operating chamber B on the two sides of the apparatus A toward the circulation chamber C in which it is heated and pushed by the fan back into the chamber B through the aerodynamic throttling partitions 4.

Again with reference to the figures, the fan is mounted on a shaft that passes through the hole H arranged on the roof of the circulation chamber C.

The assembly 1 according to the disclosure, at the region of discontinuity between areas of controlled outflow of the gas (from the circulation chamber C toward the operating chamber B), comprises an aerodynamic guide 2 that is substantially teardrop-shaped (the term "teardrop-shaped" is used to mean any tapered profile with curved and convex delimiting walls, and with the profile optionally also truncated in a lower region).

The assembly 1 comprises at least one baffle 3 that faces and is proximate to at least one respective surface 2a of the aerodynamic guide 2.

According to the disclosure, the baffle 3 has at least the face directed toward the surface 2a of the guide 2 substantially similar in shape to that of the surface 2a.

In essence, between the guide 2 and the inner face (the face directed toward the guide 2) of the baffle 3 there is a channel that has a predefined curvature (corresponding to the curvature of the surface 2a of the guide 2) within which the gas can flow without encountering discontinuities, so as to ensure a motion comparable to laminar motion.

So by analyzing the stream of gas that reaches the chamber B, it is possible to detect that it will be laminar (or that it will be comparable to such condition) given that the portion of gas that will flow through the areas of controlled outflow will be subjected to lamination (elimination of the turbulent and swirling motions) during the passing through of these, and the portion that will flow proximate to the regions of discontinuity between such areas will instead be conveyed by the guide 2 and by the baffle 3 thus minimizing the vortexes and the turbulence.

According to a particular embodiment that is particularly efficient and simple to implement, the baffle 3 can positively comprise a plate that has a shape that is substantially similar to that of the surface 2a of the aerodynamic guide 2 that it faces.

The adoption of a baffle 3 with a laminar shape structure is particularly advantageous since it ensures that the baffle 3 proper does not negatively influence the flow of gas present along its outer surface (the surface opposite from the aerodynamic guide 2); the stream of gas, in fact, flows over such outer surface without encountering unevenness or bulging that could introduce turbulence.

With particular reference to an embodiment of undoubted applicative interest, spacers for supporting the baffle 3 can be interposed between the baffle 3 and the corresponding surface 2a of the aerodynamic guide 2.

Such spacers will be integral with the surface 2a of the aerodynamic guide 2 proper.

Although the figures do not show the spacers introduced previously, it should be noted that these will be made with a tapered cross-section in order to ensure that they do not introduce turbulence into the stream of gas; similarly their thickness will also be slim (of the order of the thickness of the laminar version of the baffle 3 proper or even thinner) in order to reduce the disturbances introduced by them into the stream of gas.

With particular reference to implementation solutions that are easy to carry out, based on the adoption of conventional components, it should be noted that the areas of controlled outflow of the gas can be aerodynamic throttling partitions 4, for the reduction and containment of the turbulence in the stream of gas that passes through them.

In particular the lamination partitions 4 will comprise through channels that are intended to convey the stream of gas, evening out its motion and eliminating the turbulence and swirling motions present in it.

It should be noted that the aerodynamic throttling partitions 4 can positively be substantially parallelepiped-shaped with a thickness far lower than the length and width.

It is useful to point out that the region of discontinuity between areas of controlled outflow of the gas comprises a frame 5 for supporting contiguous lamination partitions 4.

The frame 5 thus defined is intended for resting perimetric portions of respective partitions 4.

With regard to such embodiment, it should be noted that the substantially teardrop-shaped aerodynamic guide 2 will be installed below the frame 5.

The aerodynamic guide 2 will therefore have a width similar to the width of the lower face of the frame 5 to which it is coupled.

The identical width of the guide 2 and of the frame 5 will ensure that the gas will not end up flowing in paths that comprise steps and/or points of discontinuity, therefore avoiding structural conformations that could introduce turbulence into the stream of gas proper.

Finally it should be noted that the frame 5 can preferably have a substantially lattice-like configuration, i.e. constituted by longitudinal members 6 and cross-members 7.

At the regions of intersection of the longitudinal members 6 with the cross-members 7, the aerodynamic guides 2, coupled in a lower region to the longitudinal members 6 and to the cross-members 7, will be mutually blended according to common joining lines.

It should further be noted that, according to the disclosure, at the regions of intersection of the longitudinal members 6 with the cross-members 7, the corresponding baffles 3 will also be mutually blended along connecting portions 8 that have a geometric shape that corresponds to that of the joining lines that blend the surfaces 2a of the aerodynamic guides 2 that face and are proximate to the baffles 3 proper.

Advantageously the present disclosure solves the above mentioned problems, by providing an assembly 1 for controlling and laminating a gaseous stream that minimizes the turbulence that is generated at the outflow of gas along regions of discontinuity, in particular in the regions of discontinuity between contiguous partitions 4.

The combination of the aerodynamic guides 2 and of the baffles 3 makes it possible to convey the flowing gas in such a manner as not to induce therein any turbulence or swirling, thus favoring the maintenance (or the creation) of a laminar motion.

Positively the assembly 1 according to the disclosure has a shape structure that is compatible with conventional technical solutions.

It should be noted in fact that it is possible to install the baffles 3 according to the disclosure in apparatuses A that already comprise aerodynamic guides 2 in order to increase their effects and stabilize the motion of the gas, thus making it a substantially laminar motion.

Conveniently the assembly 1 according to the disclosure is more efficient than conventional aerodynamic guides because the presence of the baffles 3 prevents fluid streamlines from detaching from them, therefore minimizing the gas component with turbulent motion.

Positively the assembly 1 according to the disclosure is easily and practically implemented, and is also low cost: such characteristics make the assembly 1 described a technical solution that is certain to be of practical application.

The disclosure thus conceived is susceptible of numerous modifications and variations, all of which are within the scope of the appended claims. Moreover, all the details may be substituted by other, technically equivalent elements.

In particular the longitudinal members 6 and the cross-members 7 of the frame 5 comprise slots 5a for the passage of the air stream: the stream is thus channeled between the internal walls of the box-like body that delimit the operating chamber B, within which pass the components to be dried and/or sterilized and/or generically treated with the stream of gas, and the walls of the aerodynamic guides 2 that face them. In essence it is evident that the stream of gas, at the frame 5, will always be conveyed in a channel defined between one of the walls of the aerodynamic guide 2 and a component that can be, in a first case, a respective baffle 3 and, in a second case, an internal wall of the box-like body that delimits the operating chamber.

In the exemplary embodiments illustrated, individual characteristics shown in relation to specific examples may in reality be interchanged with other, different characteristics, existing in other exemplary embodiments.

In practice, the materials employed, as well as the dimensions, may be any according to requirements and to the state of the art.

The disclosures in Italian Patent Application No. 102016000027865 (UB2016A001748) from which this application claims priority are incorporated herein by reference.

The invention claimed is:

1. A drying or sterilizing apparatus adapted for the circulation of a high-temperature gaseous stream, the drying or sterilizing apparatus comprises a first and a second opening for the passage of a conveyor belt on which are arranged the components to be subjected to the high-temperature gaseous stream, said first and second opening being connected with an operating chamber in which the treatment occurs, further comprising an assembly for smoothing and throttling a gaseous stream, of the type that can be installed downstream of a region of discontinuity between areas of controlled outflow of said gas and which comprises an aerodynamic guide that is substantially teardrop-shaped, the assembly further comprises at least one baffle that faces and is proximate to at least one respective surface of said aerodynamic guide, said baffle having the face directed toward said surface of said guide substantially similar in shape to that of said surface, between the guide and the inner face directed toward the guide of the baffle there being a channel with a predefined curvature, which corresponds to the curvature of the surface of the guide, the gaseous stream flowing within said channel without encountering discontinuities and with a motion comparable to laminar motion.

2. The drying or sterilizing apparatus according to claim 1, wherein said baffle comprises a plate that has a shape that is substantially similar to that of said surface of said aerodynamic guide that it faces.

3. The drying or sterilizing apparatus according to claim 1, wherein spacers for supporting said baffle are interposed between said baffle and the corresponding surface of said aerodynamic guide and are integral with said surface.

4. The drying or sterilizing apparatus according to claim 1, wherein said areas of controlled outflow of said gas are aerodynamic throttling partitions for reducing and containing turbulence in the gas stream that passes through them.

5. The drying or sterilizing apparatus according to claim 1, wherein said aerodynamic throttling partitions are substantially parallelepiped-shaped with a thickness far lower than the length and width.

6. The drying or sterilizing apparatus according to claim 1, wherein said region of discontinuity between areas of controlled outflow of said gas comprises a frame for supporting contiguous lamination partitions, said frame being intended for resting perimetric portions of respective partitions.

7. The drying or sterilizing apparatus according to claim 6, wherein said substantially teardrop-shaped aerodynamic guide is installed below said frame, said aerodynamic guide having a width similar to the width of said lower face of said frame to which it is coupled.

8. The drying or sterilizing apparatus according to claim 6, wherein said frame has a substantially lattice configuration constituted by longitudinal members and cross-members, said aerodynamic guides, coupled in a lower region to said longitudinal members and to said cross-members, being mutually blended according to common joining lines at the regions of intersection of said longitudinal members and said cross-members.

9. The drying or sterilizing apparatus according to claim 8, wherein at regions of intersection of said longitudinal members and said cross-members the corresponding baffles are mutually blended along connecting portions that have a geometric shape that corresponds to the shape of said joining lines that blend the surfaces of the aerodynamic guides that face and are proximate to said baffles.

* * * * *